(12) United States Patent
Wang et al.

(10) Patent No.: US 9,701,997 B2
(45) Date of Patent: Jul. 11, 2017

(54) COMPOSITION AND METHOD FOR IN-SYSTEM PRIMING MICROFLUIDIC DEVICES

(71) Applicant: Canon U.S. Life Sciences, Inc., Rockville, MD (US)

(72) Inventors: Ying-Xin Wang, Rockville, MD (US); Johnathan S. Coursey, Germantown, MD (US); Jason Schmidt, Arlington, VA (US); Kenton C. Hasson, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 14/746,272

(22) Filed: Jun. 22, 2015

(65) Prior Publication Data

US 2015/0284776 A1 Oct. 8, 2015

Related U.S. Application Data

(62) Division of application No. 13/221,948, filed on Aug. 31, 2011, now Pat. No. 9,061,279.

(60) Provisional application No. 61/378,543, filed on Aug. 31, 2010, provisional application No. 61/487,262, filed on May 17, 2011.

(51) Int. Cl.
*C12Q 1/68* (2006.01)
*B01L 3/00* (2006.01)

(52) U.S. Cl.
CPC ........ *C12Q 1/6806* (2013.01); *B01L 3/50273* (2013.01); *B01L 2200/10* (2013.01); *B01L 2200/146* (2013.01); *B01L 2200/147* (2013.01); *B01L 2300/0816* (2013.01); *B01L 2300/18* (2013.01); *B01L 2400/0487* (2013.01); *Y10T 137/0318* (2015.04)

(58) Field of Classification Search
CPC .................................................. C12Q 1/6806
See application file for complete search history.

(56) References Cited

U.S. PATENT DOCUMENTS

| | | |
|---|---|---|
| 6,272,939 B1 | 8/2001 | Frye et al. |
| 6,447,661 B1 | 9/2002 | Chow et al. |
| 6,524,830 B2 | 2/2003 | Kopf-Sill |
| 6,620,625 B2 | 9/2003 | Wolk et al. |
| 6,843,281 B1 | 1/2005 | Barth et al. |
| 6,960,437 B2 | 11/2005 | Enzelberger et al. |
| 7,037,416 B2 | 5/2006 | Parce et al. |
| 7,101,467 B2 | 9/2006 | Spaid |
| 7,150,999 B1 | 12/2006 | Shuck |
| 7,303,727 B1 | 12/2007 | Dubrow et al. |
| 7,390,457 B2 | 6/2008 | Schembri |
| 7,604,938 B2 | 10/2009 | Takahashi et al. |
| 7,629,124 B2 | 12/2009 | Hasson et al. |
| 7,927,865 B2 | 4/2011 | Meathrel et al. |
| 8,021,843 B2 | 9/2011 | Takagi |
| 8,163,492 B2 | 4/2012 | Unger et al. |
| 2003/0230488 A1 | 12/2003 | Lee et al. |
| 2005/0042639 A1 | 2/2005 | Knapp et al. |
| 2006/0163070 A1 | 7/2006 | Boronkay et al. |
| 2006/0211134 A1 | 9/2006 | Kennedy et al. |
| 2006/0242740 A1 | 10/2006 | Collier et al. |
| 2007/0154922 A1 | 7/2007 | Collier et al. |
| 2007/0254292 A1 | 11/2007 | Fukasawa et al. |
| 2008/0014589 A1 | 1/2008 | Link et al. |
| 2009/0111149 A1 | 4/2009 | Cao |
| 2010/0116343 A1 | 5/2010 | Weibel et al. |
| 2010/0191482 A1 | 7/2010 | Hasson et al. |
| 2011/0008223 A1 | 1/2011 | Tsao et al. |
| 2013/0209988 A1 | 8/2013 | Barber et al. |

FOREIGN PATENT DOCUMENTS

| | | |
|---|---|---|
| JP | 2004-77258 A | 3/2004 |
| JP | 2005-512031 A | 4/2005 |
| JP | 2005-192555 A | 7/2005 |
| JP | 2006-197906 A | 8/2006 |
| JP | 2008-537063 A | 9/2008 |
| JP | 2009-112278 A | 5/2009 |
| JP | 2009-270922 A | 11/2009 |
| WO | 02/085185 A2 | 10/2002 |
| WO | 02/086145 A2 | 10/2002 |
| WO | 2005/075683 A1 | 8/2005 |
| WO | 2009/120363 A1 | 10/2009 |
| WO | 2010/118427 A1 | 10/2010 |
| WO | 2010/118430 A1 | 10/2010 |

OTHER PUBLICATIONS

Weyant et al., Biotechnique, vol. 9, pp. 308-309, Sep. 1990.*
Lutz, S., et al., "Microfluidic lab-on-a-foil for nucleic acid analysis based on isothermal recombinase polymerase amplification (RPA)," Lab Chip, vol. 10, pp. 887-893 (2010).
Kopp et al., "Chemical Amplification: Continuous-Flow PCR on a Chip," Science, 280(15), pp. 1046-1048 (1998).
Lagally et al., "Single-Molecule DNA Amplification and Analysis in an Integrated Microfluidic Device," Analytical Chemistry, 73(3), pp. 565-570 (2001).
Park et al., "Cylindrical compact thermal-cycling device for continuous-flow polymerase chain reaction," Analytical Chemistry, 75, pp. 6029-6033 (2003).
Sakamoto C., et al., "Rapid and Simple Quantification of Bacterial Cells by Using a Microfluidic Device," Applied and Environmental Microbiology, vol. 71, No. 2, pp. 1117-1121 (2005).

(Continued)

*Primary Examiner* — Cynthia B Wilder (74) *Attorney, Agent, or Firm* — Rothwell, Figg, Ernst & Manbeck, P.C.

(57) ABSTRACT

The present invention relates to compositions and methods for in-system priming of microfluidic devices. Aspects of the present invention relate to compositions and methods for in-system priming of microfluidic devices utilizing a priming solution comprising adding and/or increasing concentrations of surfactant in a buffer solution.

9 Claims, 5 Drawing Sheets

(56) References Cited

OTHER PUBLICATIONS

Sekikawa T., et al., "Suppression of PCR Inhibitors Using Nonionic Surfactant for Detecting Cryptosporidium parvum DNA," Journal of Japan Society on Water Environment, vol. 31, No. 9, pp. 565-568 (2008).

* cited by examiner

COMPOSITION AND METHOD FOR IN-SYSTEM PRIMING MICROFLUIDIC DEVICES

CROSS-REFERENCE TO RELATED APPLICATION

The present application is a divisional of and claims priority to U.S. patent application Ser. No. 13/221,948, filed on Aug. 31, 2011, which claims the benefit of priority to U.S. provisional patent application Ser. No. 61/378,543, filed on Aug. 31, 2010, and U.S. provisional patent application Ser. No. 61/487,262, filed on May 17, 2011, the entire disclosures of which are incorporated herein by reference.

BACKGROUND

Field of the Invention

This invention relates to compositions and methods for in-system priming of microfluidic devices. More specifically, aspects of the present invention relate to compositions and methods for in-system priming of microfluidic devices utilizing a priming solution comprising adding and/or increasing concentrations of surfactant in a buffer solution.

Discussion of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is perhaps the most well-known of a number of different amplification techniques.

PCR is a powerful technique for amplifying short sections of deoxyribonucleic acid (DNA). With PCR, one can quickly produce millions of copies of DNA starting from a single template DNA molecule. PCR includes a three-phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Microfluidic systems are systems that have at least one microfluidic channel (a.k.a., microchannel) through which a fluid may flow, which microfluidic channel has at least one internal cross-sectional dimension, (e.g., depth, width, length, diameter) that is typically less than about 1000 micrometers. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Microfluidic devices, such as microfluidic chips, are generally primed for sample analysis to prevent, for example, air bubbles from being present in mixtures that are used to fill channels, and wells, within a microfluidic chip. The presence of air bubbles in mixtures in a chip may adversely affect the testing of chemical or biological samples using the microfluidic chip. For example, air bubbles may cause the flow of liquid within the chip to be uncontrollable. Air bubbles may also, in some systems, cause reduced thermal control. The priming of a microfluidic chip, if performed inaccurately or incorrectly, may cause an analysis performed using the microfluidic chip to be erroneous and, hence, unreliable. As it is often not known at the time a test is made whether the microfluidic chip has been primed correctly, it is important to make certain that priming procedures are accurate and precise in order to reduce the likelihood of inaccurate test results.

SUMMARY

This invention relates to compositions and methods for in-system priming of microfluidic devices that reduce the likelihood of inaccurate test results and reduces the time required for priming.

In one aspect, the invention provides a priming solution for dry priming microfluidic chips. The priming solution has high wettability, is PCR compatible and enables higher PCR efficiency. In one embodiment, the priming solution comprises a conventional 1×PCR buffer with an increased concentration of surfactant. The surfactant in the PCR buffer is increased by adding a surfactant to the PCR buffer or by increasing the concentration of the surfactant in the PCR buffer. The priming solution may also contain a dye to follow the in-system priming of a microfluidic device.

In one embodiment, the priming solution is a 1×PCR buffer in which the concentration of surfactant in the 1×PCR buffer ranges from a factor of about 5 to a factor of about 150 of the CMC for the particular surfactant(s) present in the 1×PCR buffer, preferably from a factor of about 12 to a factor of about 150, more preferably from factor of about 15 to a factor of about 135, even more preferably from a factor of about 30 to a factor of about 120. In another embodiment, priming solutions with a surfactant concentration in the lower range exhibit better drop formation. In this embodiment, the concentration of surfactant in the 1×PCR buffer ranges from a factor of about 5 to a factor of about 45 of the CMC for the particular surfactant(s) present in the 1×PCR buffer, preferably from a factor of about 12 to a factor of about 45 more preferably from factor of about 15 to a factor of about 30.

In one embodiment, the priming solution is a 1×PCR buffer in which the surfactant is Tween® 20 (polyoxyethylenesorbitan monolaurate) and the concentration is in the range of about 0.05% to about 1.0%, preferably about 0.8% to about 1.0%, more preferably from about 0.1% to about 0.9%, even more preferably from about 0.2% to about 0.8%. In another embodiment, priming solutions with a surfactant concentration in the lower range, e.g., from about 0.05% to about 0.3%, preferably from about 0.08% to about 0.3%, more preferably from about 0.1% to about 0.2%, exhibit better drop formation.

In a second aspect, the invention provides a method of in-system priming a microfluidic device. The microfluidic device may comprise one or more microfluidic chips. A microfluidic chip has at least one microchannel. In accordance with one embodiment of the invention, the method comprises the steps of applying a priming solution to a microfluidic device and applying an external pressure to flow or move the priming solution along the microchannels and through the joint of different microfluidic chips that may be used together in a microfluidic device. In one embodiment, the priming solution is a PCR buffer. In another embodiment, the priming solution is a priming solution described herein. In one embodiment, the method further comprises the step of allowing capillary pressure to flow or move the priming solution along the microfluidic channels of the microfluidic device before the external pressure is applied. In some embodiments, the microfluidic devices or microfluidic chips are pretreated with plasma to increase the hydrophilicity of the microchannel surfaces before application of the priming solution.

In accordance with another embodiment of the invention, the method comprises the steps of treating the microfluidic devices or microfluidic chips with plasma, applying a priming solution to a microfluidic device and applying an external pressure to flow or move the priming solution along the microchannels and through the joint of different microfluidic chips that may be used together in a microfluidic device. The plasma treatment increases the hydrophilicity of the microchannel surfaces. In one embodiment, the method further comprises the step of allowing capillary pressure to flow or move the priming solution along the microfluidic channels of the microfluidic device before the external pressure is applied. In some embodiments, the priming solution is a PCR buffer. In other embodiments, the priming solution is a PCR buffer having an increased surfactant concentration as described herein.

The above and other aspects and embodiments are described below with reference to the accompanying drawings.

DETAILED DESCRIPTION OF THE EXEMPLARY EMBODIMENTS

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

As used herein, the term "solution" means a liquid comprising two or more substances, and the liquid need not be a homogeneous mixture of the two or more substances.

In one aspect, the invention provides a priming solution for priming microfluidic devices. The priming composition has high wettability, is PCR compatible and enables higher PCR efficiency. In one embodiment, the priming solution comprises a conventional 1×PCR buffer with an increased concentration of surfactant. Conventional PCR buffers are well known in the art and are commercially available. PCR buffers are typically made and sold as a 10× solution so that the final dilution for the PCR reaction is 1×. As is well known to the skilled artisan, PCR buffers are optimized for the particular polymerase used in the amplification reaction. Examples of PCR buffers include, but are not limited, to the PCR buffers set forth in Table 1. In some embodiments, these buffers contain $MgCl_2$, $MgSO_4$ or Mg-acetate at concentrations well known to the skilled artisan, or they are supplemented with $MgCl_2$, $MgSO_4$ or Mg-acetate prior to use at concentrations well known to the skilled artisan. For example, a 10×PCR buffer typically contains 15 mM $MgCl_2$. The addition of co-solvents, such as DMSO (dimethyl sulfoxide), betaine (N,N,N-trimethylglycine), formamide or glycerol, to standard buffers may be useful when trying to amplify G+C-rich targets or through regions of strong secondary structure as is well known to the skilled artisan.

TABLE 1

Examples of 10X PCR Buffers

| Buffer | Composition, 10X | pH |
|---|---|---|
| 1 | 375 mM Tris-HCl, 200 mM $(NH_4)_2SO_4$, 0.1% Tween ® 20 | 8.8 |
| 2 | 670 mM Tris-HCl, 150 mM $(NH_4)_2SO_4$, 0.1% Tween ® 20 | 8.8 |
| 3 | 1.0M Tris-HCl, 200 mM $(NH_4)_2SO_4$, 0.1% Tween ® 20 | 8.4 |
| 4 | 600 mM Tris-HCl, 170 mM $(NH_4)_2SO_4$, 0.1% Tween ® 20 | 9.0 |
| 5 | 500 mM Tris-HCl, 200 mM $(NH_4)_2SO_4$ | 8.4 |
| 6 | 500 mM Tricin-KOH, 170 mM $(NH_4)_2SO_4$, 0.1% Tween ® 20 | 8.7 |
| 7 | 500 mM Tricin-KOH, 150 mM $(NH_4)_2SO_4$ | 8.7 |
| 8 | 500 mM Tris-HCl, 500 mM KCl | 8.4 |
| 9 | 400 mM Tris-HCl, 500 mM NaCl | 7.5 |
| 10 | 500 mM Tricin-KOH, 450 mM K-acetate, 5% DMSO, 40% glycerol | 8.7 |
| 11 | 500 mM Tris-HCl | 9.5 |
| 12 | 100 mM Tris-HCl, 50 mM DTT (dithiothreitol) | 7.5 |
| 13 | 100 mM Tris-HCl, 100 mM KCl | 8.3 |
| 14 | 100 mM Tris-HCl, 500 mM KCl, 1% Triton ® X-100 | 8.9 |
| 15 | 100 mM Tris-HCl, 500 mM KCl | 8.0 |
| 16 | 400 mM Tris-HCl, 650 mM K-glutamate, 1% Triton ® X-100 | 8.7 |
| 17 | 400 mM Tris-HCl, 650 mM K-acetate, 1% Triton ® X-100 | 8.7 |
| 18 | 600 mM Tris-HCl, 60 mM $(NH_4)_2SO_4$, 100 mM KCl | 8.3 |
| 19 | 500 mM Tris-HCl, 50 mM $(NH_4)_2SO_4$, 100 mM KCl | 9.0 |
| 20 | 200 mM Tris-HCl, 100 mM $(NH_4)_2SO_4$, 100 mM KCl, 1% Triton ® X-100 | 8.9 |
| 21 | 1M Tris-HCl, 100 mM $(NH_4)_2SO_4$, 100 mM KCl, 1% Triton ® X-100 | 8.7 |
| 22 | 200 mM Tris-HCl, 100 mM $(NH_4)_2SO_4$, 100 mM KCl, 1% Triton ® X-100, 1 mg/ml BSA (bovine serum albumin) | 8.7 |
| 23 | 100 mM Tris-HCl, 500 mM KCl, 1% Triton ® X-100 | 8.3 |
| 24 | 100 mM Tris-HCl, 500 mM KCl, 0.1% (w/v) gelatin | 8.3 |
| 25 | 100 mM Tris-HCl, 500 mM KCl, 15 mM $MgCl_2$, 0.01% (w/v) gelatin | 8.3 |
| 26 | 100 mM Tris-HCl, 500 mM KCl, 0.8% Nonidet P-40 | 8.8 |
| 27 | 100 mM Tris-HCl, 500 mM KCl, 15 mM $MgCl_2$, 0.8% Nonidet P-40 | 8.8 |
| 28 | 750 mM Tris-HCl, 200 mM $(NH_4)_2SO_4$, 0.1% Tween ® 20 | 8.8 |
| 29 | 750 mM Tris-HCl, 200 mM $(NH_4)_2SO_4$, 20 mM $MgCl_2$, 0.1% Tween ® 20 | 8.8 |
| 30 | 200 mM Tris-HCl, 100 mM $(NH_4)_2SO_4$, 100 mM KCl, 1% (v/v) Triton ® X-100, 1 mg/ml BSA, 20 mM $MgSO_4$ | 8.8 |
| 31 | 200 mM Tris-HCl, 500 mM KCl, 15 mM $MgCl_2$ | 8.5 |
| 32 | 200 mM Tris-HCl, 50 mM $(NH_4)_2SO_4$, 200 mM KCl | 8.3 |

As is evident from the examples of PCR buffers in Table 1, each PCR buffer contains a buffering agent which is compatible with the PCR reaction, such as Tris(hydroxymethylaminoethane) or Tricine (N-(tri(hydroxymethyl)methyl)glycine), at a concentration ranging from, for example, 10 mM to 100 mM for a 1×PCR buffer. As is also evident from the examples of PCR buffers in Table 1, 1×PCR buffers may optionally contain a salt, such as, $(NH_4)_2SO_4$, KCl, NaCl, K-acetate and K-glutamate or combinations thereof, at a concentration ranging from 10 mM to 65 mM for a 1×PCR buffer. In addition, as shown by the examples of PCR buffers in Table 1, 1×PCR buffers may optionally contain DTT, DMSO, glycerol, BSA and gelatin. Furthermore, as described herein, PCR buffers may also optionally contain $MgCl_2$, betaine or formamide. As is further evident from the examples of PCR buffers in Table 1, 1×PCR buffers may optionally contain a surfactant such as a Tween® surfactant (Tween® 20 for example) or a Triton® surfactant (Triton® X-100 (octylphenol ethylene oxide condensate) for example) at a low concentration. For example, for 1×PCR buffer 1, the Tween® 20 is present at a concentration of 0.01%, and for 1×PCR buffer 14, the Triton® X-100 is present at a concentration of 0.1%. These percentages for surfactants are based on a volume to volume basis.

It has been found that conventional PCR buffers used at a 1× concentration for priming microfluidic devices were not adequate to completely prime the surfaces of the microfluidic devices. It was hypothesized that PCR buffer could be modified to adequately prime the surfaces of microfluidic devices by increasing the wettability of a priming solution. In accordance with the present invention, the wettability of the PCR buffer is increased by adding a surfactant or by increasing the concentration of the surfactant in the PCR buffer. The higher surfactant concentration in the buffer was found not only to give the priming solution a high wettability, but surprisingly also to enable a higher PCR efficiency in the PCR amplification reaction. In addition, it was found that a rinsing step could be eliminated for priming microfluidic devices when the priming solution of the present invention was used. Elimination of a rinsing step simplifies the priming of microfluidic devices.

In accordance with aspects of the present invention, a PCR buffer conventionally used by the skilled artisan, such as those described above, are modified to either increase the surfactant concentration in PCR buffers which contain a surfactant or to add a surfactant to PCR buffers which do not contain a surfactant to prepare the priming solution of the present invention. For priming microfluidic devices in accordance with one embodiment of the present invention, the PCR buffer used for the priming solution is a 1×PCR buffer. A 1×PCR buffer modified as described herein is sometimes referred to as a 1× priming solution.

The concentration of surfactant in the priming solution is achieved by adding surfactant to a conventional PCR buffer that is to be used for preparing the priming solution. In one embodiment, the PCR buffer to be used contains some surfactant. In this embodiment, sufficient surfactant is added to bring the concentration to the levels described herein. Although any surfactant or mixture of surfactants described herein can be added in this embodiment, typically the same surfactant as initially used in the PCR buffer can be used. In another embodiment, the PCR buffer to be used does not contain a surfactant. In this embodiment, any surfactant or mixture of surfactants described herein can be added to a conventional PCR buffer. As described herein, the priming solution is a 1×PCR buffer having a modified surfactant concentration. Alternatively, the priming solution of the present invention is prepared by making a 1×PCR buffer having the desired components of the buffer as illustrated herein. Such buffers are prepared in a manner well known to the skilled artisan. Stock solutions of the priming solution are also contemplated by the present invention. Any suitable stock solution, such as 2×-100× or more, of the priming solution can be made and then diluted to a 1× concentration prior to use. For example, a 10× stock solution of the priming solution can be made and then diluted to the 1× priming solution described herein prior to use in dry priming a microfluidic chip.

In accordance with aspects of the present invention, any surfactant or mixture of surfactants can be used in the priming solution as long as the priming solution meets the requirements described herein. Specifically, the priming solution must have high wettability and must be PCR compatible. In addition, it is desirable if the priming solution also enhances PCR efficiency. Polysorbate surfactants, such as the Tween® surfactants, and octylphenol ethoxylate surfactants, such as the Triton® surfactants are particularly useful in preparing priming solutions in accordance with the present invention. Any of the Tween® surfactants well known to the skilled artisan or any of the Triton® surfactants well known to the skilled artisan can be used in accordance with the present invention. Tween® 20 surfactant and Triton® X-100 surfactant typically used in PCR buffers are particularly useful in the present invention. In addition to these classes of surfactants, other classes of surfactants that can be used include, but are not limited to, ethoxylated aliphatic alcohol surfactants, polyoxyethylene surfactants (such as Nonidet P-40), carboxylic ester surfactants, polyethylene glycol ester surfactants, anhydrosorbitol ester and it's ethoxylated derivatives surfactants, fatty acid glycol ester surfactants, carboxylic amide surfactants, monoalkanolamine condensate surfactants and polyoxyethylene fatty acid amide surfactants. Mixtures or combinations of any of the surfactants described herein can also be used in preparing the priming solutions in accordance with the present invention.

In one embodiment, the increased concentration of surfactant in the priming solution is a factor of the critical micelle concentration (CMC). As is known to the skilled artisan, the CMC is an important characteristic of a surfactant and is defined as the concentration of surfactants above which micelles form and almost all additional surfactants added to the system go to micelles. The CMC of various surfactants are well known to the skilled artisan. See, for example, Detergents Properties and Applications (www.sigmaaldrich.com/img/assets/15402/Detergent_Selection_Table.pdf). In one embodiment, the concentration of surfactant in the 1×PCR buffer ranges from a factor of about 5 to a factor of about 150 of the CMC for the particular surfactant(s) present in the 1×PCR buffer, preferably from a factor of about 12 to a factor of about 150, more preferably from factor of about 15 to a factor of about 135, even more preferably from a factor of about 30 to a factor of about 120. It has been found that priming solutions with a surfactant concentration in the lower range exhibit better drop formation. In this embodiment, the concentration of surfactant in the 1×PCR buffer ranges from a factor of about 5 to a factor of about 45 of the CMC for the particular surfactant(s) present in the 1×PCR buffer, preferably from a factor of about 12 to a factor of about 45 more preferably from factor of about 15 to a factor of about 30. A suitable amount of surfactant to use in the priming solution can be readily determined for each surfactant as described herein by comparison with the concentrations of Tween® 20 described herein that have been found useful for the priming solutions of the present invention. In one embodiment, the surface tension, contact angle and drop formation are examined as described herein to select a suitable surfactant concentration of surfactant to use in the priming solution for priming microfluidic devices.

The priming solution may also contain a dye or marker to monitor the in-system priming of a microfluidic device. Any suitable fluorescent or non-fluorescent dye may be used. The dye may be part of an aqueous or organic system. The dye may be used in water alone or a buffer solution or may optionally be included in the 1×PCR buffer. Suitable fluorescent dyes include but are not limited to sulforhodomine, Alexa Fluor, LightCycler Red, Oregon Green, FAM, fluorescein, Rhodamine, CyDyes (Cy3 and Cy5 for example), Texas Red, Cal Fluor, Atto, or Kiton Red. Examples of suitable non-fluorescent dyes include synthetic or natural dyes, food dye, azo dyes as well as anthraquinone and triarylmethane dyes. In some embodiments, red fluorescent dyes, such as Alexa Fluor 647, Atto655, Atto680 and Atto647N are used. The concentration of dye present in the priming solution should be adjusted based on system requirements including but not limited to dye solubility, quantum yield, detector sensitivity, and size/shape of the region interrogated on the microfluidic device. The dye or marker may be present in the priming solution from about 5 µM to about 500 µM, preferably from about 10 µM to about 100 µM, and more preferably from about 30 µM to about 50 µM. In some embodiments, Alexa Fluor 647 is used at a concentration from about 30 µM to about 50 µM.

In one embodiment, the surfactant is Tween® 20 and the concentration in the priming solution is in the range of about 0.05% to about 1.0%, preferably about 0.08% to about 1.0%, more preferably from about 0.1% to about 0.9%, even more preferably from about 0.2% to about 0.8%. All surfactant percentages are expressed as volume/volume (v/v) herein. It has been found that priming solutions with a surfactant concentration in the lower range, e.g., from about 0.05% to about 0.3%, preferably from about 0.08% to about 0.3%, more preferably from about 0.1% to about 0.2%, exhibit better drop formation. The correlation of the % concentration of Tween® 20 to the CMC is shown in Table 2.

TABLE 2

Correlation of % Concentration to Factor of CMC for Tween ® 20

| % Concentration | Factor of CMC |
|---|---|
| 0.05 | 7.5 |
| 0.08 | 12 |
| 0.1 | 15 |
| 0.2 | 30 |
| 0.3 | 45 |
| 0.8 | 120 |
| 0.9 | 135 |
| 1.0 | 150 |

Note:
Based on a CMC for Tween ® 20 of 0.06 mM (Detergents Properties and Applications).

In one embodiment, a priming solution in accordance with the present invention comprises the components shown in Table 3.

TABLE 3

Priming Solution Components and Amounts

| Component | Amount | Preferred Amount | More Preferred Amount | Most Preferred Amount |
|---|---|---|---|---|
| Tris-HCl | 10 mM-100 mM | 25 mM-75 mM | 50 mM | 50 mM |
| KCl | 10 mM-50 mM | 25 mM-50 mM | 50 mM | 5 mM |
| betaine | 0.5-2M | 0.5-1.5M | 1M | 1M |
| DMSO | 1-5% (v/v) | 1-3% | 2% | 2% |
| Tween ® 20 | 0.08%-1.0% | 0.1%-0.9% | 0.1%-0.8% | 0.12% |

Note:
% are volume/volume.

In a second aspect, the present invention provides a method of in-system priming a microfluidic device. The microfluidic device may comprise one or more microfluidic chips. In accordance one embodiment, the method comprises the steps of applying the priming solution to a microfluidic device and applying an external pressure to move or flow the priming solution along the microfluidic channels and through the joint(s) of different microfluidic chips that may be used together in a microfluidic device. In one embodiment, the method further comprises the step of allowing capillary pressure to move or flow the priming solution along microfluidic channels of the microfluidic device before the application of the external pressure. It was found that a rinsing step could be eliminated for priming microfluidic devices when the priming solution of the present invention was used. Elimination of a rinsing step simplifies the priming of microfluidic devices.

The priming solution of the present invention can be used to dry prime microfluidic devices. Microfluidic devices are well known in the art and typically include one or more microfluidic chips and typically utilize sippers or pipettes. The microfluidic chips have at least one microchannel, and may include any number of channels within the dimensions of the microfluidic chip. Examples of microfluidic devices known in the art include, but are not limited to, Chow et al. (U.S. Pat. No. 6,447,661), Kopf-Sill (U.S. Pat. No. 6,524,830), Spaid (U.S. Pat. No. 7,101,467), Dubrow et al. (U.S. Pat. No. 7,303,727), Schembri (U.S. Pat. No. 7,390,457), Schembri (U.S. Pat. No. 7,402,279), Takahashi et al. (U.S. Pat. No. 7,604,938), Knapp et al. (U.S. Patent Application Publication No. 2005/0042639), and Hasson et al. (U.S. Patent Application Publication No. 2010/0191482). Each of these patents or patent application publications is incorporated herein by reference.

In addition to these microfluidic devices, the priming solution of the present invention can be used to prime microfluidic devices described in copending applications: U.S. patent application Ser. No. 12/758,482 filed on Apr. 12, 2010 (U.S. Patent Application Publication No. 2011/0008223), International patent application No. PCT/US2010/030762 filed on Apr. 12, 2010 (International Publication No. 2010/118427), International patent application No. PCT/US2010/30766 filed on Apr. 12, 2010 (International Publication No. 2010/118430), U.S. provisional patent application No. 61/378,722 filed on Aug. 31, 2010, which describes method, devices and systems for fluid mixing and chip interfaces, and U.S. patent provisional application No. 61/378,824 filed on Aug. 31, 2010, which describes a system and method for rapid serial processing of multiple nucleic acid assays. Each of these copending applications is incorporated herein by reference.

Furthermore, the priming solution of the present invention can be used in conjunction with microfluidic priming devices or modules known in the art. Examples of microfluidic priming devices or modules known in the art include, but are not limited to, Frye et al. (U.S. Pat. No. 6,272,939), Barth et al. (U.S. Pat. No. 6,843,281), Lee et al. (U.S. Patent Application Publication No. 2003/0230488), Boronkay et al. (U.S. Patent Application Publication No. 2006/0163070) and Kennedy et al. (U.S. Patent Application Publication No. 2006/0211134). Each of these patents or patent application publications is incorporated herein by reference.

In accordance with one embodiment, the in-system priming method of the present invention comprises a method for dry priming a microfluidic device. This dry priming is in contrast to wet priming, such as described by Shuck (U.S. Pat. No. 7,250,999). According to one embodiment of the present invention, the priming solution is first applied to a microfluidic device or to the component chips or modules of the microfluidic device.

The method of application utilized is dependent on the type of microfluidic device that is being used. In one embodiment, the microfluidic device includes an inverted sipper. In this embodiment, a drop of the priming solution is applied to the top of the inverted sipper by a pipette, which is typically robotically controlled. For this embodiment, it is desirable to use a priming solution which has good drop formation, i.e., priming solutions with a lower amount of surfactant in accordance with the present invention as described herein. In another embodiment, the microfluidic device includes a sipper assembly. In this embodiment, the priming solution is added to a sipper assembly reservoir or well. The priming solution is applied to the microfluidic device by the sipper contacting the priming solution in the reservoir or well. For this embodiment, drop formation is not as important and thus priming solutions containing any amount of surfactant in accordance with the present invention as described herein can be utilized. In an additional embodiment, the microfluidic device simply contains wells to which the priming solution is added. The wells are in contact with the microchannels such that the priming solution is drawn into the microchannels. For this embodiment, drop formation is not as important and thus priming solutions containing any amount of surfactant as described herein can be utilized.

After the priming solution is applied to the microfluidic device, an external pressure is applied to the microfluidic device to drive or move the priming solution along the microchannels of the microfluidic device The application of the external pressure, which may be a positive pressure or a negative pressure, is somewhat dependent on the configuration of the microfluidic device that is being primed. Typically, a negative pressure is applied to the vent wells and to the waste wells of the microfluidic device. The external pressure is typically applied until the priming solution appears in the waste wells, i.e., the external pressure is applied until the priming solution has been completely driven, flowed or moved through the microchannels. In one embodiment, a negative pressure from about −14.7 psi (−1.012328 bar) to about −0.01 psi (−0.000689 bar), preferably, from about −10.0 psi (−0.689548 bar) to about −0.1 psi (−0.00689 bar), more preferably from about −1.2 psi (−0.082737 bar) to about −0.4 psi (−0.027579 bar), and most preferably about −1.0 psi (−0.068948 bar), is applied to the vent wells, and a negative pressure from about −14.7 psi (−1.012328 bar) to about −0.01 psi (−0.000689 bar), preferably, from about −10.0 psi (−0.689548 bar) to about −0.1 psi (−0.00689 bar), more preferably from about −1.2 psi (−0.082737 bar) to about −0.4 psi (−0.027579 bar), and most preferably about −1.0 psi −0.068948 bar), is applied to the waste wells. In one embodiment, a microfluidic system is designed to have solution delivered by pipette tips to the sipper and then a negative pressure is applied to the vent and waste wells to draw or move liquid through the microchannels. In this embodiment, a positive pressure cannot be applied directly through sipper. However, a positive pressure could be applied for this embodiment by connecting a manifold over the inlet (e.g., sipper assembly). Peristaltic pumps connected to the manifold could then increase the static pressure to push the priming solution through the device. Positive pressures from about 0.001 psi (0.0000689 bar) to about 150 psi (10.34212 bar) may be used, preferably from about 0.01 psi (0.000689 bar) to 15 psi (1.034212), and more preferred pressures range from 0.1 psi (0.006895 bar) to about 1.5 psi (0.103421 bar). In another embodiment, the priming solution is delivered manually to the waste wells, and then a positive pressure is applied on the waste wells to drive the priming solution through the microchannels to the sipper and to the vent wells. In this embodiment, the priming solution must then be manually removed from the wells prior to use of the microfluidic device. In this embodiment, the positive pressure ranges and values are as described above.

In one embodiment, after the priming solution is applied to the microfluidic device, the priming solution is first allowed to flow or move along the microchannels of the microfluidic device by capillary pressure before the external pressure is applied. The priming solution is allowed to flow or move through the microchannels by capillary pressure as long as it continues to move or flow. In one embodiment, once the movement by capillary pressure ceases, an external pressure is then applied to further drive or flow the solution along the microchannels and through the joint(s) of different chips, if present in the microfluidic device. In one embodiment, the flow or movement of the priming solution by capillary pressure occurs for about 30 seconds to about 5 minutes, preferably for about 30 seconds to about 2 minutes. After the priming solution has flowed along the microchannels by capillary pressure, the external pressure is applied as described above.

In one embodiment, the priming solution includes a dye or marker as described herein. The presence of the dye or marker is useful for monitoring the in-system priming of the microfluidic devices. Monitoring of the in-system priming may be performed by a priming control system. The priming control system may include an optical system. The optical system may include an imaging device (e.g., CMOS camera) and an illumination means (e.g., LEDs to excite fluorescent dye or white light for visible dyes). The priming control system may use the optical system to collect information about the progress of the priming. In one embodiment, the priming control system may monitor the dye or marker tracked priming solution to determine when the movement due to capillary pressure has ceased. In another embodiment, the priming control system may monitor the dye or marker tracked priming solution to determine if priming was successful. The dye may be used to determine if a certain feature of the microfluidic chip has primed. In one embodiment, an LED in a microfluidic system is used to illuminate the dye in the priming solution in microchannel.

To further improve the in-system priming of microfluidic device, the device can be pretreated with plasma to increase the hydrophilicity of the microchannel surface. The plasma treatment not only increases the priming success rate but also reduces priming time. In accordance with this embodiment, the entire fully fabricated microfluidic device having microchannels is treated with plasma. The fully fabricated microfluidic device may be comprised of a single microfluidic chip or module or multiple microfluidic chips or modules. The microfluidic device is treated before it is placed in the system for performing intended assays. Plasma generators are well known in the art and include, but are not limited to, a Harrick Plasma Cleaner, Model PDC100, plasma reactor 790 Series, Plasma-Therm, Inc., Florida, USA; microwave-plasma-generator (13.56 MHz, Plasma Technology, Rottenburg, Germany. In certain embodiments, plasma is applied to the microfluidic device in which all of the wells, reservoirs and microchannels are open for a length of time sufficient to treat all of the surfaces of the microfluidic device, typically about 4 to about 7 minutes at high power, more typically about 5 minutes at high power. The generated oxygen plasma penetrates into the surfaces of the channels, wells, etc. and introduces the silanol group to the surface and changes the surface properties to hydrophilic. Priming microfluidic devices in accordance with the present invention can be performed faster with a plasma pretreatment.

According to another embodiment of the present invention, a microfluidic device or the component chips or modules of the microfluidic device are first treated with plasma as described herein. A priming solution is then applied to the microfluidic device or the component chips or modules of the microfluidic device as described herein. In some embodiments, the priming solution is a PCR buffer. In other embodiments, the priming solution is a PCR buffer having an increased surfactant concentration as described herein. After the priming solution is applied, an external pressure is applied as described herein to move the priming solution through the microchannels. In one embodiment, after the priming solution is applied to the microfluidic device, the priming solution is first allowed to flow or move along the microchannels of the microfluidic device by capillary pressure as described herein before the external pressure is applied. In this embodiment, once the movement by capillary pressure ceases, an external pressure is then applied to further drive or flow the solution along the microchannels and through the joint(s) of different chips, if present in the microfluidic device. In one embodiment, the priming solution includes a dye or marker as described herein. The presence of the dye or marker is useful for monitoring the in-system priming of the microfluidic devices as described herein.

Figure 1:
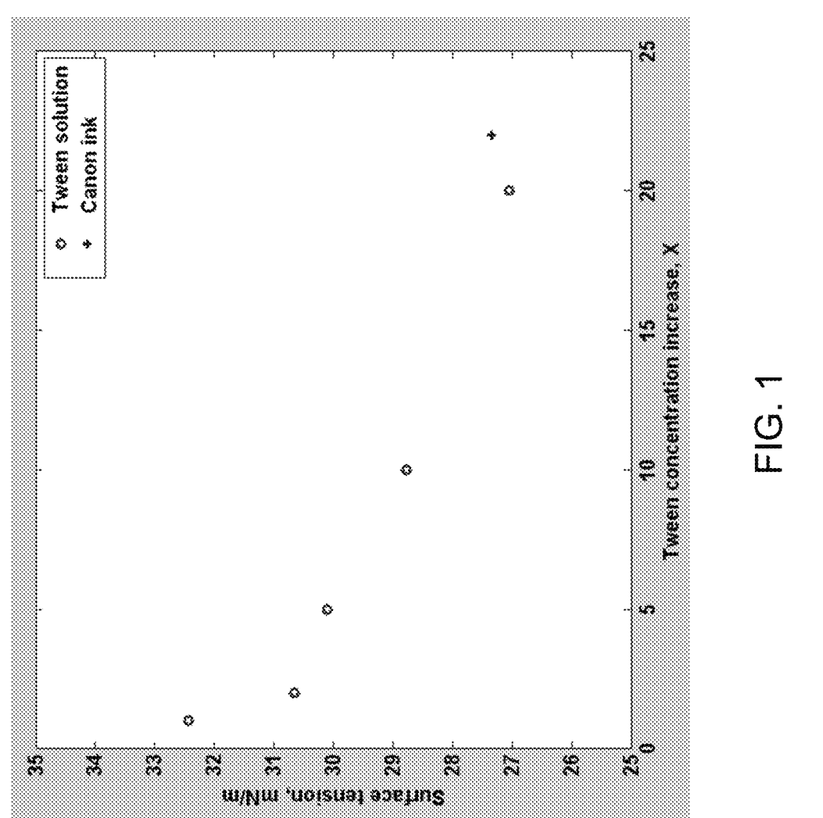
FIG. 1 illustrates the change in surface tension of a priming solution as a function of increasing Tween® 20 surfactant concentration.
Figure 2:
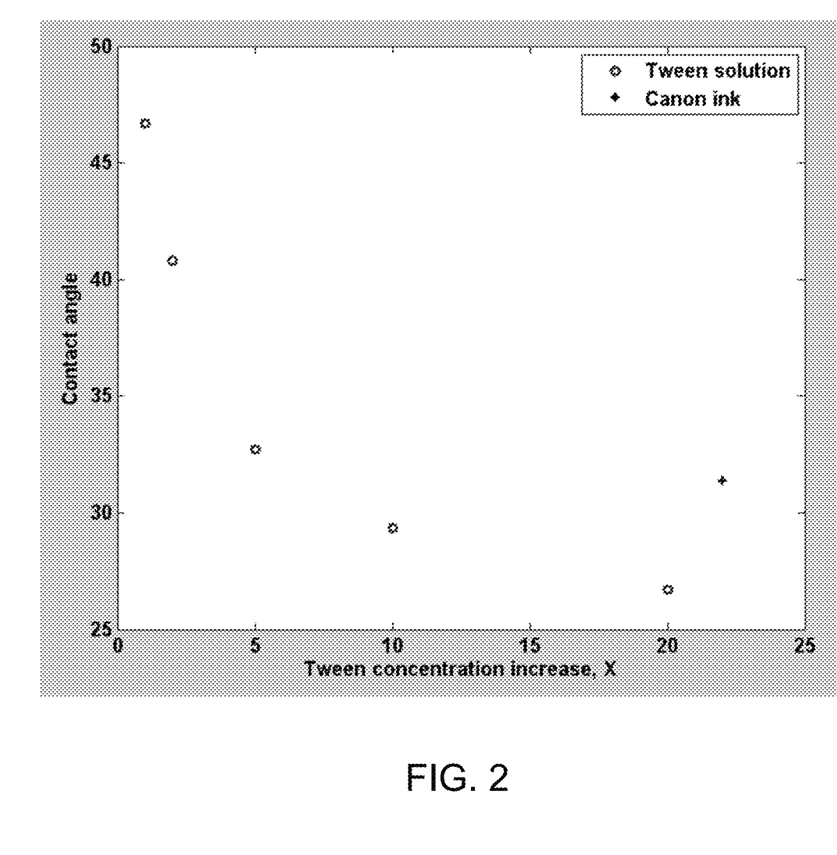
FIG. 2 illustrates the change in contact angle of a priming solution as a function of increasing Tween® 20 surfactant concentration.

Aspects of the present invention can be illustrated by the following non-limiting examples. A 1×PCR buffer typically used for a PCR amplification reaction was prepared comprising 50 mM Tris, pH 8, 50 mM KCl, 1 M Betaine, 2% DMSO and 0.04% Tween® 20. Modified 1×PCR buffers were prepared in which the concentration of Tween® 20 was 2×, 5×, 10× and 20× of the original concentration of Tween® 20. Thus, the Tween® 20 concentrations in the modified 1×PCR buffers were 0.08%, 0.2%, 0.4% and 0.8%, respectively. The increased concentrations of Tween® 20 in the modified 1×PCR buffers were tested for their ability to reduce the surface tension and contact angle of the 1×PCR buffer. The change in the surface tension as a factor of the increased concentration of Tween® 20 in the modified 1×PCR buffer is shown in FIG. 1. The change in the contact angle as a factor of the increased concentration of Tween® 20 in the modified 1×PCR buffer is shown in FIG. 2. The measurements in FIG. 2 were taken at 1 minute after the drop was placed on a polymethylmethacrylate (PMMA) surface. The change in the surface tension and contact angle of the modified 1×PCR buffer was compared to a Canon ink that was known to have excellent wettability properties. In addition to surface tension and contact angle, the modified 1×PCR buffers were also tested for drop formation. Suitable concentrations of other surfactants can be determined by comparing surface tension, contact angle and drop formation with the Tween® concentrations described herein.

Figure 3:
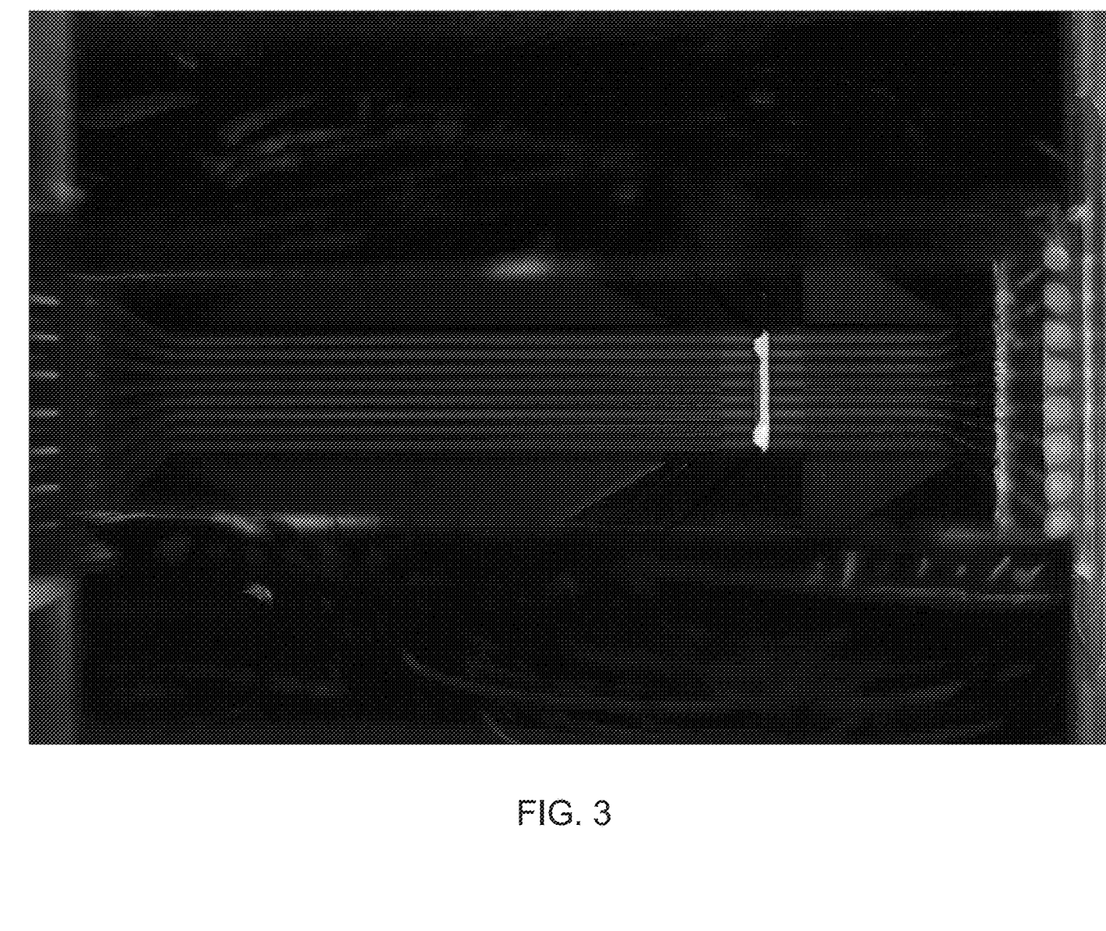
FIG. 3 shows that a priming solution primes all eight microchannels of a microfluidic chip as evidenced by the microchannels fluorescing from fluorescent dye (as shown in whitish color in center of figure) contained in the priming solution according to one embodiment of the present invention.

As shown in FIGS. 1 and 2, the surface tensions and contact angles of the 10× and 20× Tween® 20 1×PCR buffers are closer to the Canon ink. The 2× and 5× Tween® 20 1×PCR buffers have better drop formation. On the basis of these tests, the 5× Tween® 20 solution was chosen for testing in the priming of microfluidic devices or microfluidic chips which use an inverted sipper due to its high wettability and better drop formation. FIG. 3 shows that the 5× solution successfully primed the microfluidic chips in a system which utilizes an inverted sipper as shown by the fluorescing microchannels (seen as the whitish color) in the center of the figure. In this test, the microchannels fluoresced red because the priming solution contained a red fluorescent dye (e.g., Alexa 647) and a red excitation LED was turned on. The observed fluorescence indicates that all microchannels were successfully primed. While a red fluorescent dye was included in this embodiment for monitoring the priming process, other dyes (fluorescent and otherwise) are contemplated as well.

Figure 4:
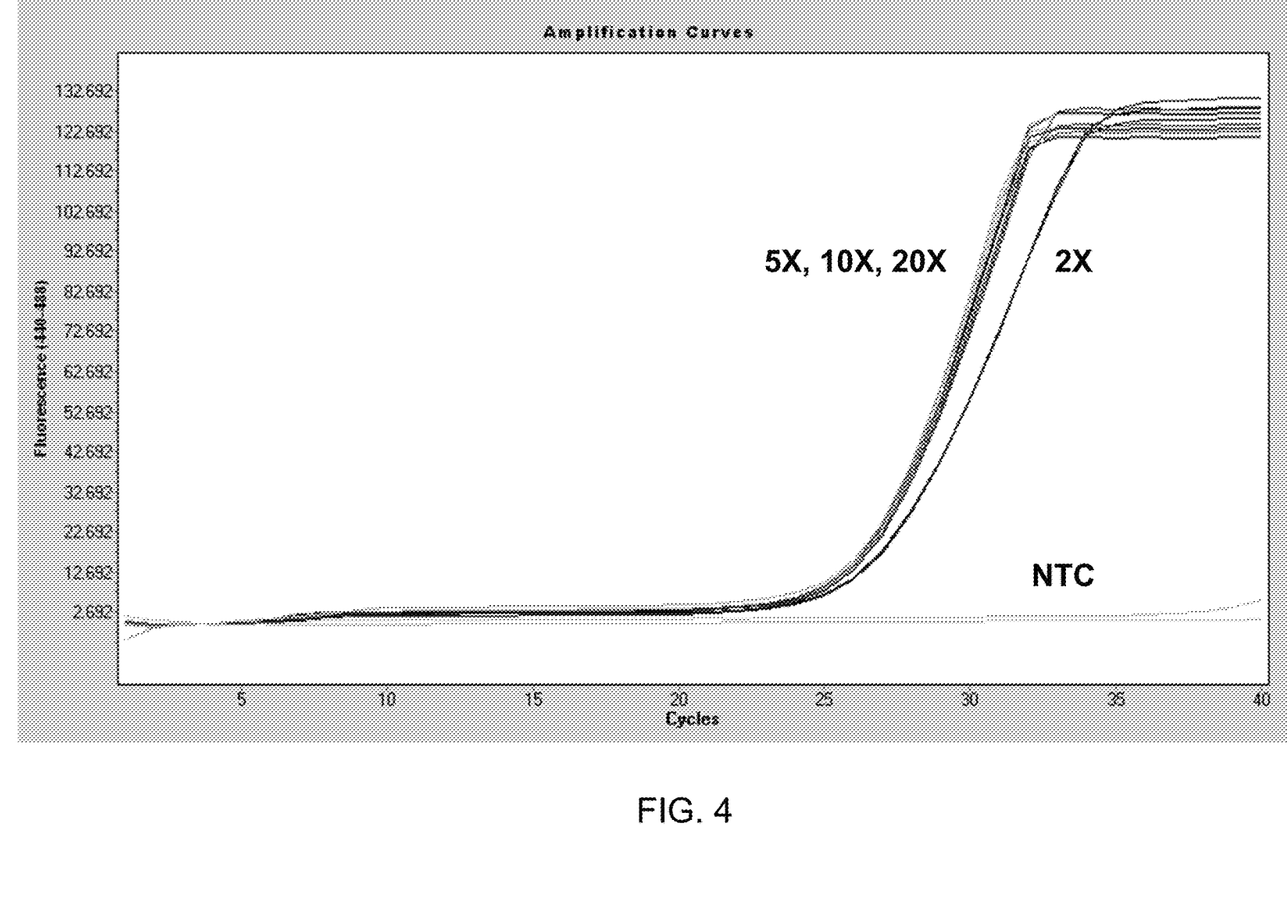
FIG. 4 shows amplification curves for amplifying a test nucleic acid using a modified PCR buffer.
Figure 5:
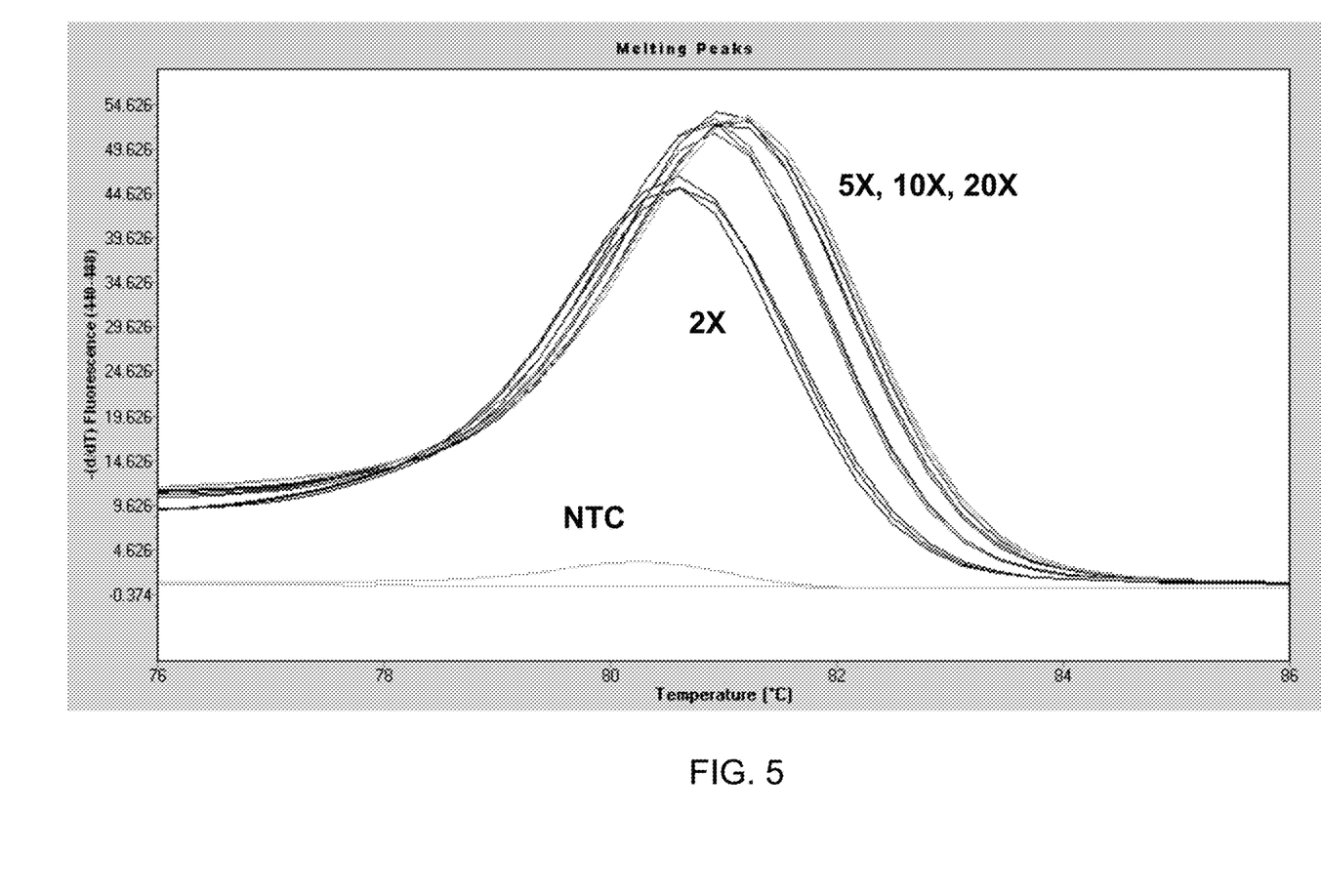
FIG. 5 shows melting curves for the amplified test nucleic acid using the modified PCR buffers illustrated in FIG. 4.

To test the effect of an increased surfactant concentration on PCR, a test nucleic acid was amplified using a buffer with modified surfactant concentrations. In this experiment, a 2×PCR buffer was used for testing 2×, 5×, 10× and 20× Tween® 20 concentrations. The amplifications were carried out using a LightCycler® 480 Real-Time PCR System from Roche. The test nucleic acid was a weight standard nucleic acid. The amplification used the following conditions: pre-amplification: 95° C. for 1 min; 40 cycles of amplification: 95° C. for 5 sec, 62° C. for 5 sec and 72° C. for 5 sec; post-amplification: 37° C. for 10 sec and 95° C. for 10 sec. The thermal melting was performed by ramping from 55° C. to 95° C. using 1° C./second. The effects of an increased concentration of Tween® 20 on the amplification and the thermal melt analysis are shown in FIG. 4 and FIG. 5, respectively. As shown in FIG. 4, the amplification reaction is more efficient with increased surfactant as evidenced by fewer cycles being required to reach maximum amplification. FIG. 5 shows that better melting curves are obtained with increased surfactant. These results demonstrate that PCR buffer modified to include increased surfactant concentration are PCR compatible and enhance the efficiency of the PCR reaction.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. In addition, recitation of ranges of values herein are merely intended to serve as a shorthand method of referring to all separate ranges falling within the range, unless otherwise indicated, and each separate range is incorporated into the specification as if it were individually recited herein. For example, if the range 10-15 is disclosed, then the ranges 10-14, 10-13, 10-12, 10-11, 11-15, 11-14, 11-13, 11-12, 12-15, 12-14, 12-13, 13-15, 13-14 and 14-15 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A priming solution comprising:
   a 1×PCR buffer containing a surfactant, wherein a concentration of the surfactant is from a factor of about 5 to a factor of about 150 of the critical micelle concentration (CMC) of the surfactant; and
   a dye or a marker at concentration from 5 μM to about 500 μM for monitoring the priming solution.

2. The priming solution of claim 1, wherein the concentration of surfactant is from a factor of about 5 to a factor of about 45 of the critical micelle concentration (CMC) of the surfactant.

3. The priming solution of claim 1, wherein the surfactant is selected from the group consisting of polysorbate surfactants, octylphenol ethoxylate surfactants, ethoxylated aliphatic alcohol surfactants, polyoxyethylene surfactants, carboxylic ester surfactants, polyethylene glycol ester surfactants, anhydrosorbitol ester and its ethoxylated derivatives surfactants, fatty acid glycol ester surfactants, carboxylic amide surfactants, monoalkanolamine condensate surfactants, polyoxyethylene fatty acid amide surfactants and combinations thereof.

4. The priming solution of claim 1, wherein the surfactant is a polysorbate surfactant.

5. The priming solution of claim 4, wherein the surfactant is polyoxyethylenesorbitan monolaurate.

6. The priming solution of claim 5, wherein the concentration of polyoxyethylenesorbitan monolaurate is in the range from about 0.05% to about 1.0%.

7. The priming solution of claim 5, wherein the concentration of polyoxyethylenesorbitan monolaurate is in the range from about 0.05% to about 0.3%.

8. The priming solution of claim 1, wherein the surfactant is an octylphenol ethoxylate surfactant.

9. The priming solution of claim 8, wherein the surfactant is octylphenol ethylene oxide condensate.

* * * * *